US012715834B2

(12) United States Patent
Myrdek et al.

(10) Patent No.: US 12,715,834 B2
(45) Date of Patent: Aug. 25, 2026

(54) ETHER CARBOXYLIC ACID COMPOSITION

(71) Applicant: Kao Chemicals GmbH, Emmerich (DE)

(72) Inventors: Thomas Myrdek, Emmerich (DE); Reinout Van der Veen, Emmerich (DE); Michael Stapels, Emmerich (DE); Masakatsu Takahashi, Barberà del Vallés (ES)

(73) Assignee: Kao Chemicals GmbH, Emmerich (DE)

( * ) Notice: Subject to any disclaimer, the term of this patent is extended or adjusted under 35 U.S.C. 154(b) by 1052 days.

(21) Appl. No.: 17/787,439

(22) PCT Filed: Dec. 23, 2020

(86) PCT No.: PCT/EP2020/087771

§ 371 (c)(1),
(2) Date: Jun. 20, 2022

(87) PCT Pub. No.: WO2021/130316

PCT Pub. Date: Jul. 1, 2021

(65) Prior Publication Data

US 2023/0059894 A1 Feb. 23, 2023

(30) Foreign Application Priority Data

Dec. 27, 2019 (EP) .................................... 19219824

(51) Int. Cl.
*C07C 59/125* (2006.01)
*C07C 51/367* (2006.01)

(52) U.S. Cl.
CPC .......... *C07C 59/125* (2013.01); *C07C 51/367* (2013.01)

(58) Field of Classification Search
None
See application file for complete search history.

(56) References Cited

U.S. PATENT DOCUMENTS

| | | | |
|---|---|---|---|
| 3,992,443 | A | 11/1976 | Springmann |
| 4,625,057 | A | 11/1986 | Springmann |
| 6,034,257 | A | 3/2000 | Oftring et al. |
| 7,179,452 | B2 | 2/2007 | Muller et al. |
| 9,909,081 | B2 | 3/2018 | Scanlon et al. |
| 2005/0197261 | A1 | 9/2005 | Leinweber |
| 2006/0047141 | A1 | 3/2006 | Behler et al. |
| 2009/0023623 | A1 | 1/2009 | Yamamoto et al. |
| 2011/0034359 | A1 | 2/2011 | Rabbat |
| 2011/0154724 | A1 | 6/2011 | Martyak et al. |
| 2014/0315769 | A1 | 10/2014 | Rabbat |
| 2015/0011455 | A1 | 1/2015 | Moragas Arjant et al. |
| 2017/0009172 | A1 | 1/2017 | Bender et al. |

FOREIGN PATENT DOCUMENTS

| | | |
|---|---|---|
| CN | 106883833 | 10/2019 |
| CS | 256198 | 8/1987 |
| EP | 1329214 | 7/2003 |
| EP | 1479754 | 11/2004 |
| EP | 1739161 | 1/2007 |
| EP | 2612652 | 7/2013 |
| JP | H03-103500 | 4/1991 |
| WO | 2002081381 | 10/2002 |
| WO | 2009040370 A1 | 4/2009 |
| WO | 2016093291 | 6/2016 |

OTHER PUBLICATIONS

Office Action in corresponding Chinese Patent Application Serial No. 202080090414.1, dated May 27, 2024 (English translation attached).

Amarego, et al., "Common physical techniques used in purification", Purification of Laboratory Chemicals, 7th Edition, 2013, pp. 1-70.

*Primary Examiner* — Amy C Bonaparte
(74) *Attorney, Agent, or Firm* — Hovey Williams LLP; Crissa A. Cook

(57) ABSTRACT

The present invention relates to a composition comprising at least an ether carboxylic acid. The present invention also relates to the method for obtaining of the composition and to the use of the composition in industrial applications such as engine oil compositions, metal working compositions, lubricant compositions and oil fuel compositions.

5 Claims, No Drawings

ETHER CARBOXYLIC ACID COMPOSITION

FIELD OF THE INVENTION

The present invention relates to a composition comprising at least an ether carboxylic acid. The present invention also relates to the method for obtaining of the composition and to the use of the composition in industrial applications such as engine oil compositions, metal working compositions, lubricant compositions and oil fuel compositions.

STATE OF THE ART

Ether carboxylic acids are organic carboxylic acids which, in addition to the carboxyl group, have one or more ether bridges. Ether carboxylic acids, or the alkali metal or amine salts thereof, are known to be mild detergents with a high lime soap dispersion capacity. They are used as a multifunctional tool in formulations, being used, for instance, as cleaner, emulsifier, dispersant, solubiliser or hydrotrope. Therefore, they are used in laundry detergent and cosmetic formulations, as well as in industrial applications.

Relevant properties for ether carboxylic acids and methods of obtaining them are the ease of handling for the user, residual salt content, water content, selectivity and degree of carboxymethylation as well as the obtaining a product with lower raw material cost and with a better environmentally friendly process.

Ether carboxylic acids are used in different applications due to their relevant properties. For instance, they are used in cosmetic applications due its mildness, easy application, good detergency and cleansing ability, flowability, being homogeneous at room temperature and exhibiting good foaming properties. Ether carboxylic acids are also of special interest in industrial applications, such as in metal working fluids, engine oils, oil field applications, drilling fluids or lubricant applications due to its characteristics of good solubility behaviour, viscosity, thermal stability, hygroscopicity, foam control ability, lime soap dispersion, electrolyte stability, hydrotropic properties, good emulsifier, water hardness stability, improved lubricity and corrosion inhibition.

There are already known methods of preparation of ether carboxylic acids. The two main methods of preparation are the Williamson ether synthesis or carboxyalkylation, which consists in the alkylation of alcohol or fatty alcohol alkoxylates with chloroacetic acid derivatives; and the second method of preparation, which consists in the oxidation of the same starting materials with various reagents (atmospheric oxygen, hypochlorite, chlorite) under catalysis with various catalysts.

Williamson ether synthesis is the most common process to obtain ether carboxylic acids. It can be performed in a solid/solid process, that wherein the starting materials (chloroacetic acid and the alkaline source) are in a solid form.

EP1574560 describes a process for the preparation of ether carboxylic acid compounds, wherein the process comprises the steps of alkylating an oxoalkylated alcohol with sodium chloroacetate and sodium hydroxide in a solid state, then converting the obtained ethercarboxylic acid salt to the free ethercarboxylic acid by addition of an acid, and afterwards freeing the water from the obtained ether carboxylic acid, without washing, by distillation under reduced pressure, and finally removing the precipitated metal salts by filtration to obtain a product with low values of residual water content and residual salt content.

Williamson ether synthesis can also be performed in a liquid/liquid process, wherein the starting materials (chloroacetic acid and the alkaline source) are in a liquid form. U.S. Pat. No. 4,625,057 describes a process for the obtention of ether carboxylic acids comprising the reaction of ether alcohols with an aqueous solution of a stoichiometric amount of free chlorocarboxylic acid and twice the stoichiometric amount of an aqueous base. The water content is maintained at 0.3-1.5% wt. and the process results in increased selectivity.

Moreover, U.S. Pat. No. 3,992,443 describes a mixed process, wherein alcohols, preferably ethoxylated alcohols are carboxymethylated by reacting a mixture of the ethoxylated alcohol and a salt of chloroacetic acid with an alkali hydroxide, wherein the alkali hydroxide can be used both in solid form and in aqueous solution. Equimolar mixtures of starting alcohol and chloroacetate salt are generally employed; however molar excess of the alcohol or molar excess of the chloroacetate salt can be used, depending on the intended effect.

There is however still a need for ether carboxylic acids that meet the requirements of industrial applications, particularly water hardness stability and improved lubricity.

The present invention provides a composition comprising at least an ether carboxylic acid, a process of preparation of said ether carboxylic acid and its use in engine oil applications, metal working applications, lubricant applications and oil fuel applications, wherein said compositions comprising the ether carboxylic acid fulfill requirements of water hardness stability and improved lubricity.

SUMMARY OF THE INVENTION

The first object of the present invention is a composition comprising an ether carboxylic acid.

Another object of the present invention is the process to obtain said composition.

Another object of the present invention is the use of said composition in industrial applications such as engine oils, metal working compositions, lubricant compositions and oil fuel compositions.

A further object of the present invention is a method for obtaining an engine oil composition, a metal working composition, a lubricant composition and oil fuel composition, based on the application of a composition according to the invention to these compositions.

DETAILED DESCRIPTION OF THE INVENTION

The main object of the present invention is a composition comprising an ether carboxylic acid of formula (I).

Ether Carboxylic Acid:

The ether carboxylic acid is represented by formula (I):

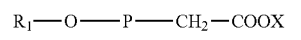

Formula (I)

wherein $R_1$ is a linear or branched alkyl or alkenyl chain having from 1 to 30 carbon atoms, preferably from 3 to 24 carbon atoms, more preferably from 6 to 22 carbon atoms; P comprises an average of n units of $—(CH_2CH_2O)—$ and/or an average of m units of $—(CH_2CHR_2O)—$ or $—(CHR_2CH_2O)—$ and/or an average of q units of $—(CH_2CHR_3O)—$ or $—(CHR_3CH_2O)—$, wherein n represents a number within the range of 0 to 50, m represents a number within the range of 0 to 50 and q represents a number within the range of 0 to 50; and the sum of n+m+q represents the average alkoxylation degree which corresponds to a number from 1 to 100; $R_2$ represents a group and $R_3$ represents a $—CH_2CH_3$ group; and X represents a hydrogen atom or a cation selected from the group of an alkali metal, an alkaline earth metal, ammonium, an alkylammonium, an alkanolammonium or a glucammonium.

The ether carboxylic acid of formula (I) is usually a mixture of compounds comprising different molecules satisfying formula (I), but with different meanings of R1, m, n, and d. The indicated ranges for m, n, and p above and hereinbelow define the average number of units in this mixture.

In an embodiment of the present invention, P comprises an average of n units of $—(CH_2CH_2O)—$ and/or an average of m units of $—(CH_2CHR_2O)—$ or $—(CHR_2CH_2O)—$ and/or an average of p units of $—(CH_2CHR_3O)—$ or $—(CHR_3CH_2O)—$, wherein n represents a number within the range of 0 to 50, preferably within the range of 0 to 30, more preferably within the range of 0 to 25, even more preferably within the range of 0 to 20; m represents a number within the range of 0 to 50, preferably within the range of 0 to 30, more preferably within the range of 0 to 25, even more preferably within the range of 0 to 20; q represents a number within the range of 0 to 50, preferably within the range of 0 to 30, more preferably within the range of 0 to 25, even more preferably within the range of 0 to 20; and the sum of n+m+q represents the average alkoxylation degree which corresponds to a number from 1 to 100, preferably from 1 to 50, more preferably from 1 to 30, even more preferably from 1 to 25.

In one embodiment of the present invention the ether carboxylic acid of formula (I) can be ethoxylated and/or propoxylated and/or butoxylated. Both the ether carboxylic acid according to formula (I) comprising ethylene and/or propylene oxide and/or butylene oxide groups in separate blocks and the ether carboxylic acid according to formula (I) comprising ethylene oxide and/or propylene oxide and/or butylene oxide groups randomly distributed can be used in the compos dons according the invention.

In an embodiment of the present invention, P comprises an average of n units of $—(CH_2CH_2O)—$, wherein n represents a number within the range of 0 to 50, preferably within the range of 1 to 30, more preferably within the range of 1 to 25, even more preferably within the range of 1 to 20; and m and q represent 0, and the sum of n+m+q represents the average alkoxylation degree which corresponds to a number from 1 to 50, preferably from 1 to 30, more preferably from 1 to 25 even more preferably from 1 to 20.

In another embodiment of the present invention, P comprises an average of m units of $—(CH_2CHR_2O)—$ or $—(CHR_2CH_2O)—$, wherein m represents a number within the range of 0 to 50, preferably within the range of 1 to 30, more preferably within the range of 1 to 25, even more preferably within the range of 1 to 20; and n and q represent 0, and the sum of n+m+q represents the average alkoxylation degree which corresponds to a number from 1 to 50, preferably from 1 to 30, more preferably from 1 to 25, even more preferably from 1 to 20.

In another embodiment of the present invention, P comprises an average of q units of $—(CH_2CHR_3O)—$ or $—(CHR_3CH_2O)—$, wherein q represents a number within the range of 0 to 50, preferably within the range of 1 to 30, more preferably within the range of 1 to 25, even more preferably within the range of 1 to 20; and n and m represent 0, and the sum of represents the average alkoxylation degree which corresponds to a number from 1 to 50, preferably from 1 to 30, more preferably from 1 to 25, even more preferably from 1 to 20.

In another embodiment of the present invention, P comprises an average of n units of $—(CH_2CH_2O)—$ and in average of m units of $—(CH_2CHR_2O)—$ or $—(CHR_2CH_2O)—$, wherein n represents a number within the range of 0 to 50, preferably within the range of 1 to 25, more preferably within the range of 1 to 20, even more preferably within the range of 1 to 15; m represents a number within the range of 0 to 50, preferably within the range of 1 to 25, more preferably within the range of 1 to 20, even more preferably within the range of 1 to 15; q represents 0, and the sum of n+m+q represents the average alkoxylation degree which corresponds to a number from 1 to 100, preferably from 1 to 50, more preferably from 1 to 35, even more preferably from 1 to 25.

In one embodiment of the present invention the ether carboxylic acid of formula (I) comprises ethylene oxide and propylene oxide groups. The ether carboxylic acid compound of formula (I) comprising ethylene oxide and propylene oxide groups in separate blocks, and the ether carboxylic acid compound of formula (I) comprising ethylene oxide and propylene oxide groups randomly distributed can be used in the compositions according to the invention.

In a preferred embodiment of the present invention the ether carboxylic of formula (I) comprises ethylene oxide and propylene oxide groups. The ether carboxylic acid of formula (I) comprising ethylene oxide and propylene oxide groups in separate blocks can be used in the compositions according to the invention.

In another preferred embodiment of the present invention the ether carboxylic acid of formula (I) comprises ethylene oxide and propylene oxide groups. The ether carboxylic acid of formula (I) comprises ethylene oxide and propylene oxide groups in separate groups, wherein ethylene oxide groups are closer to the carboxyl group. Preferred compounds of this embodiment are those of Formula (Ia);

Formula (Ia)

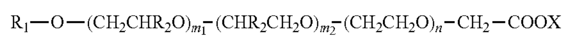

$$R_1—O—(CH_2CHR_2O)_{m1}—(CHR_2CH_2O)_{m2}—(CH_2CH_2O)_n—CH_2—COOX$$

Wherein $R_1$, $R_2$, X, and n have the same meaning as in Formula (I), and wherein m1 and m2 each represent a number within the range of 0 to 50, with m1+m2 being a number within the range of 0 to 50.

In another embodiment of the present invention, P comprises an average of m units of $—(CH_2CHR_2O)—$ or $—(CHR_2CH_2O)—$ and an average of q units of $—(CH_2CHR_3O)—$ or $—(CHR_3CH_2O)—$, wherein m represents a number within the range of 0 to 50, preferably within the range of 1 to 25, more preferably within the range of 1 to 20, even more preferably within the range of 1 to 15; q represents a number within the range of 0 to 50, preferably within the range of 1 to 25, more preferably within the range of 1 to 20, even more preferably within the range of 1 to 15; n represents 0, and the sum of n+m+q represents the average alkoxylation degree which corresponds to a number from 1 to 100, preferably from 1 to 50, more preferably from 1 to 35, even more preferably from 1 to 25.

In another embodiment of the present invention, P comprises an average of n units of $—(CH_2CH_2O)—$ and an average of q units of $—(CH_2CHR_3O)—$ or $—(CHR_3CH_2O)—$, wherein n represents a number within the range of 0 to 50, preferably within the range of 1 to 25, more preferably within the range of 1 to 20, even more preferably within the range of 1 to 15; q represents a number within the range of 0 to 50, preferably within the range of 1 to n 25, more preferably within the range of 1 to 20, even more preferably within the range of 1 to 15; m represents 0, and the sum of n+m+q represents the average alkoxylation degree which corresponds to a number from 1 to 100, preferably from 1 to 50, more preferably from 1 to 35, even more preferably from 1 to 25.

In another embodiment of the present invention, a $R_1$ near or branched alkyl containing 1 to 30 carbon atoms or a linear alkenyl containing 1 to 30 carbon atoms and from 1 to 3 double bonds; preferably the alkyl or alkenyl contains 4 to 28 carbon atoms, more preferably 6 to 18 carbon atoms.

In another embodiment of the present invention, $R_1$ is a linear or branched alkyl or a linear alkenyl derived from natural fats and oils, as well as of synthetic origin. Preferred fats and oils include palm oil, coconut oil, sunflower oil, rapeseed oil, castor oil, olive oil, soybean oil; animal fat such as tallow, bone oil, fish oil, hardened oils and semi-hardened oils thereof, and mixtures thereof. As a result of its natural origin, the fats and oils may contain a great variety of alkyl and/or alkenyl groups, said groups being linear or branched, saturated or unsaturated.

In another embodiment of the present invention, the ether carboxylic acid of formula (I) are derived from $C_3$-$C_{30}$ fatty alcohols, preferably from $C_4$-$C_{28}$ fatty alcohols, which are preferably derived from natural fats and oil as well as synthetic origin. Preferred fats and oils include palm oil, coconut oil, sunflower oil, rapeseed oil, castor oil, olive oil, soybean oil; animal fat such as tallow, bone oil, fish oil, hardened oils and semi-hardened oils thereof; and mixtures thereof. As a result of its natural origin, the fatty alcohols may contain a great variety of alkyl and/or alkenyl groups, said groups being linear or branched, saturated or unsaturated.

In a particularly preferred embodiment the ether carboxylic acid of formula (I) is one wherein n represents a number within the range of 0 to 10, m represents a number within the range of 0 to 8, q represents 0, and the sum of n+m+q represents the average alkoxylation degree which corresponds to a number from 2 to 12.

In another preferred embodiment, the ether carboxylic acid compound of formula (I) is one wherein m represents a number within the range of 0 to 10, preferably of 1 to 8, more preferably of 1 to 5, n and represent 0, and the sum of n+m+q represents the average alkoxylation degree which corresponds to a number from 1 to 10, preferably from 1 to 8, more preferably from 1 to 5.

Preparation Process

The ether carboxylic acid of formula (I) according to the invention can be prepared by a process comprising at least the steps of the alkoxylation of a fatty alcohol to obtain a mixture comprising alkoxylated fatty alcohols, and the alkylation of the mixture with a halocarboxylic acid.

i. Alkoxylation of Fatty Alcohols

The alkoxylation of alcohols can be carried out under standard conditions known by persons skilled in the art. For example, the polyalkoxylated group is obtained by the addition of ethylene oxide and/or propylene oxide and/or butylene oxide to fatty alcohols, mostly with an alkaline catalyst such as NaOH, KOH, $Na_2CO_3$, $K_2CO_3$, $KOCH_3$ and its solutions in methanol, or $NaOCH_3$ and its solutions in methanol giving a broad polyalkoxylated oxide distribution (broad alkoxylation degree). For special applications the alkoxylation can be catalysed by Lewis acids or by using metallic Na or NaH to achieve a narrow range distribution (narrow alkoxylation degree). Suitable examples of available alkoxylated alcohols are AKYPO© ROX RLM 80V (Laureth-8), AKYPO© ROX RLM 22 (Laureth-2), AKYPO© FOX RS-0602N (alkoxylated stearyl alcohol), AKYPO© ROX RC-0960N (alkoxylated cetyl alcohol), all of them marketed by Kao Chemicals Europe.

The product resulting from the alkoxylation reaction comprises a mixture of alkoxylated fatty alcohol (ethoxylated and/or propoxylated and/or butoxylated) and non-alkoxylated fatty alcohol.

In an embodiment of the present invention, the order of addition of ethylene oxide and/or propylene oxide and/or butylene oxide to fatty alcohols is random.

In another embodiment of the present invention, first propylene oxide and/or butylene oxide group are added, followed by the addition of ethylene oxide group.

In an embodiment of the present invention, the alkoxylated fatty alcohol is represented by formula (II):

Formula (II)

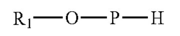

wherein $R_1$ is a linear or branched alkyl or alkenyl chain having from 1 to 30 carbon atoms, preferably from 3 to 24 carbon atoms, more preferably from 6 to 22 carbon atoms; P comprises an average of n units of —$(CH_2CH_2O)$— and/or an average of m units of —$(CH_2CHR_2O)$— or —(CH2CH2O)— and/or an average of q units of —$(CH_2CHR_3O)$— or —$(CHR_3CH_2O)$—; wherein n represents a number within the range of 0 to 50, m represents a number within the range of 0 to 50 and e represents a number within the range of 0 to 50; and the sum of n+m+q represents the average alkoxylation degree which corresponds to a number from 1 to 60; $R_2$ represents a —$CH_3$ group and $R_3$ represents a —$CH_2CH_3$ group.

Suitable fatty alcohols according to formula (II) are n-butanol, n-hexanol, n-octanol, 2-ethylbutanol, 2-methylpentanol, 2-ethylhexanol, 2-methylheptanol, n-decanol, 2-methyl-4-nonanol, 3,7-dimethyl-3-octanol, 3,7-dimethyl-1-octanol, 3,6-dimethyl-3-octanol, lauryl alcohol (1-dodecanol), myristyl alcohol (1-tetradecanol), cetyl alcohol (1-hexadecanol), palmitoleyl alcohol (cis-9-hexadecan-1-ol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E, 15-E-octadecatrien-1-ol), ricinoleyl alcohol (12-hydroxy-9-octadecen-1-ol), arachidyl alcohol (1-eicosanol), behenyl alcohol (1-docosanol), erucyl alcohol (cis-13-docosen-1-ol) or mixtures thereof; and the corresponding alkoxylated (ethoxylated and/or propoxylated and/or butoxylated) alcohols thereof or mixtures thereof.

In an embodiment of the present invention, the fatty alcohol is cetyl alcohol, stearyl alcohol, oleyl alcohol or mixtures thereof, the corresponding alkoxylated (ethoxylated and/or propoxylated and/or butoxylated) alcohols thereof or mixtures thereof.

In another embodiment of the present invention, fatty alcohols are derived from natural fats and oils, as well as of synthetic origin. Preferred fats and oils include palm oil, coconut oil, sunflower oil, rapeseed oil, castor oil, olive oil, soybean oil; animal fat such as tallow, bone oil, fish oil, hardened oils and semihardened oils thereof, and mixtures thereof. As a result of its natural origin, the fats and oils may contain a great variety of alkyl and/or alkenyl groups, said groups being linear or branched, saturated or unsaturated.

In an embodiment of the present invention, the alkoxylated fatty alcohol compound of formula (II) can be ethoxylated and propoxylated. The fatty alcohol compound comprising ethylene oxide and propylene oxide groups in separate blocks and the fatty alcohol compound comprising ethylene oxide and propylene oxide groups randomly distributed can be used in the invention.

In an embodiment of the present invention, the alkoxylated fatty alcohol compound of formula (II) can be ethoxylated and propoxylated. The fatty alcohol compound comprising ethylene oxide and propylene oxide groups in separate blocks can be used in the compositions according to the invention.

In another embodiment of the present invention, the alkoxylated fatty alcohol compound of formula (II) comprises ethylene oxide and propylene oxide groups in separate groups, wherein ethylene oxide groups are closer to free hydroxyl group. Preferred compounds of this embodiment are those of Formula (IIa):

Formula (Ia)

$$R_1-O-(CH_2CHR_2O)_{m1}-(CHR_2CH_2O)_{m2}-(CH_2CH_2O)_n-CH_2-COOX$$

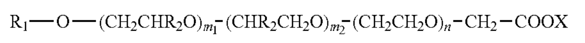

Wherein $R_1$, $R_2$, and n have the same meaning as in Formula (I), and wherein m1 and m2 each represent a number within the range of 0 to 50, with m1+m2 being a number within the range of 0 to 50.

ii. Carboxyalkylation Reaction:

The alkoxylated (ethoxylated and/or propoxylated and/or butoxylated) fatty alcohol is reacted with a halocarboxylic acid, wherein before the addition of the halocarboxylic acid into the reaction there is an initial feeding of alkaline solution into the mixture, and wherein the initial feeding of the alkaline solution comprises from 5% wt. to 50% wt. of total amount of alkaline solution, preferably from 3% to 25% wt. of total amount of alkaline solution.

In the carboxyalkylation reaction the molar ratio between the halocarboxylic acid and the alkali salt in the alkaline solution is higher than 1:2.05 to 1:3, preferably from 1:2.15 to 1: 2.5.

In an embodiment of the present invention, the halocarboxylic acid is a $C_2$ to $C_5$, chlorocarboxylic acid. In a preferred embodiment of the present invention the halocarboxylic acid is monochloroacetic acid.

In an embodiment of the present invention, the carboxyalkylation reaction is a carboxymethylation reaction.

In an embodiment of the present invention, the halocarboxylic acid is an aqueous solution of the halocarboxylic acid.

In another embodiment of the invention, the concentration of the halocarboxylic acid in the aqueous solution is from 60% to 85% wt. In another embodiment of the invention, the concentration of the halocarboxylic acid in the aqueous solution is from 70% to 80% wt.

In an embodiment of the present invention, the aqueous halocarboxylic acid is an aqueous $C_2$ to $C_5$ chlorocarboxylic acid. In a preferred embodiment of the present invention the aqueous halocarboxylic acid is aqueous monochloroacetic acid.

In an embodiment of the present invention, the alkaline solution is an aqueous alkaline solution.

In another embodiment of the invention, the concentration of alkaline solution is an alkali metal hydroxide or an alkaline earth metal hydroxide in the aqueous alkaline solution is from 30% to 60% wt. In another embodiment of the present invention, the concentration of alkaline solution is an alkali metal hydroxide or an alkaline earth metal hydroxide in the aqueous alkaline solution from 40 to 55% wt.

In another embodiment of the present invention, the alkaline solution is an alkali metal hydroxide or an alkaline earth metal hydroxide such as sodium hydroxide, potassium hydroxide, magnesium hydroxide, lithium hydroxide, barium hydroxide. In an embodiment of the invention, preferred alkaline solutions are sodium hydroxide and potassium hydroxide.

In a preferred embodiment of the present invention, all reagents in carboxyalkylation reaction are in aqueous solution.

In an embodiment of the present invention, the dosage time of the initial feeding of the alkaline solution comprises from 1 to 50% of total time of the carboxyalkylation reaction, preferably from 5 to 25% of total time of the carboxyalkylation reaction.

In an embodiment of the present invention, the alkoxylated (ethoxylated and/or propoxylated and/or butoxylated) reacted with a halocarboxylic acid is prepared in-situ, before the carboxyalkylation reaction.

In another embodiment of the present invention, the alkoxylated (ethoxylated and/or propoxylated and/or butoxylated) alcohol reacted with a halocarboxylic acid is obtained commercially.

According to the present invention, the aqueous alkaline solution and the halocarboxylic acid are preferably continuously fed to the reaction.

The continuous feeding of the alkaline solution begins prior to the feeding of the halocarboxylic acid, but is continued during the feeding of the halocarboxylic acid.

In an embodiment of the present invention, the process comprises a step iii) after the carboxyalkylation reaction, to convert the alkali metal ethercarboxylate to the free ether carboxylic acid by acidification with any acid, preferably HCl.

The composition that results from the carboxyalkylation reaction comprises ether carboxylic acid, unreacted substances in the process for obtaining the ether carboxylic acid, such as not carboxyalkylated alkoxylated fatty alcohol, free fatty alcohol, esters or by-products from the same reaction such as sodium glycolate, sodium diglycolate, substances having vapour pressure, high boiling substances, oligomer and polymer as well as inorganic halides such as sodium chloride, and water.

In an embodiment of the present invention, the process further comprises a step iv) comprising a washing step.

In an embodiment of the present invention, the process further comprises a step v) comprising a distillation step.

In another embodiment of the present invention, the conversion degree of ether carboxylic acid is higher than 40%, preferably higher than 60%, more preferably higher than 70%, even more preferably higher than 80%.

Conversion degree calculated as the moles of ether carboxylic acid obtained divided per moles of initial alkoxylated fatty alcohol used.

According to the described procedure, it is possible to quantify the amount of oxidizable substances present in the reaction mixture, that is, the amount of oxygen that can be consumed by reactions in a solution. This chemical oxygen demand (COD) can be expressed in mass of oxygen consumed over volume of solution, which Si units are milligrams of $O_2$ per litre (mg $O_2$/L).

In an embodiment of the present invention, the chemical oxygen demand of the solution is measured in the water phase obtained after step iv) comprising a washing step.

In an embodiment of the present invention, the chemical oxygen demand of the solution after the process to obtain of the ether carboxylic acid is lower than 45000 mg $O_2$/L, preferably lower than 40000 mg $O_2$/L.

In an embodiment of the present invention, the content of inorganic salts after the washing step is below 1 wt %.

In an embodiment of the present invention, the content of water in the organic phase after the washing phase is below 5 wt. %

Composition of the Invention:

The composition of the present invention contains the ether carboxylic acid of formula (I). This composition can be prepared by the method described above.

In another embodiment of the present invention, the composition comprises at least 40% by weight, preferably at least 60% wt, more preferably at least 70% wt, even more preferably at least 80% wt. of ether carboxylic acid of formula (I) with respect to the total active material of the composition of the invention.

It is understood as active material as the group of specific components responsible for a specific action; in the scope of the present application the active material is all the surfactants present in the composition.

In a preferred embodiment of the present invention, the composition comprises an ether carboxylic acid of formula (I), wherein P comprises n units of $—(CH_2CH_2O)—$, and n represents a number within the range of 0 to 50, preferably within the range of 1 to 30, more preferably within the range of 1 to 25, even more preferably within the range of 1 to 20; m and q represent 0, and the sum of n+m+q represents the average alkoxylation degree which corresponds to a number from 1 to 50, preferably from 1 to 30, more preferably from 1 to 25, even more preferably from 1 to 20, and wherein the composition comprises at least 40% by weight, preferably at least 60% wt, more preferably at least 70 wt, even more preferably at least 80 wt. of ether carboxylic acid compound of formula (I) with respect to the total active material of the composition of the invention.

In another preferred embodiment of the present invention, the composition comprises of ether carboxylic acid of formula (I), wherein P comprises an average of m units of $—(CH_2CHR_2O)—$ or $—(CHR_2CH_2O)—$, and m represents a number within the range of 0 to 50, preferably within the range of 1 to 30, more preferably within the range of 1 to 25, even more preferably within the range of 1 to 20; n and q represent 0, and the sum of n+m+q represents the average alkoxylation degree which corresponds to a number from 1 to 50, preferably from 1 to 30, more preferably from 1 to 25, even more preferably from 1 to 20, and wherein the composition comprises at least 40% by weight, preferably at least 60% wt, more preferably at least 70% wt, even more preferably at least 80% wt. of ether carboxylic acid compound of formula (I) with respect to the total active material of the composition of the invention.

In another preferred embodiment of the present invention, the composition comprises an ether carboxylic acid of formula (I), wherein P comprises an average of n units of $—(CH_2CH_2O)—$ and an average of m units of $—(CH_2CHR_2O)—$ or $—(CHR_2CH_2O)—$, n represents a number within the range of 0 to 50, preferably within the range of 1 to 25, more preferably within the range of 1 to 20, even more preferably within the range of 1 to 15; m represents a number within the range from 0 to 50, preferably within the range of 1 to 25, more preferably within the range of 1 to 20, even more preferably within the range of 1 to 15; q represents 0, and the sum of n+m+q represents the average alkoxylation degree which corresponds to a number from 1 to 100, preferably from 1 to 50, more preferably from 1 to 35, even more preferably from 1 to 25, and wherein the composition comprises at least 40% by weight, preferably at least 60% wt, more preferably at least 70% wt, even more preferably at least 80% wt. of ether carboxylic acid compound of formula (I) with respect to the total active material of the composition of the invention.

The compositions of the present invention have good water hardness stability and improved lubricity.

Moreover, the composition s the present invention also preferably fulfill the requirements of solubility, viscosity, thermal stability, hygroscopicity, foam control ability, lime soap dispersion, electrolyte stability, hydrotropic properties, good emulsifier and corrosion inhibition.

Use of Compositions According to the Invention in Industrial Applications:

The compositions according to the invention can be used in industrial applications, such as in engine oils, lubricants, metal working fluids or oil field applications.

The use of compositions comprising ether carboxylic acids in industrial applications can be explained due to its foam control ability, lime soap dispersion, high thermal stability, electrolyte stability, hydrotropic properties, solubilizing properties, good emulsifier, water hardness stability as well as improved lubricity and corrosion inhibition.

The compositions comprising ether carboxylic acid of formula (I) according to the invention can be used as additives in formulations for industrial applications. That is, the compositions according to the invention can be used as additives in engine oil formulations, in lubricant formulations, in metal working fluids formulations or oil field formulations.

In an embodiment of the present invention, the compositions comprising ether carboxylic acids of formula (I) according to the invention can be used as additives in formulations for industrial applications, wherein the amount of composition is from 0.1 to 10% wt., preferably from 1 to 5% wt. of total weight of the formulation for industrial applications.

Another aspect of the present invention is the use of the composition according to the invention in engine oils.

Another aspect of the present invention is the use of the composition according to the invention in lubricants.

Another aspect of the present invention is the use of the composition according to the invention in metal working fluids.

Another aspect of the present invention is the use of the composition according to the invention in oil field.

Another aspect of the present invention is a process of preparation of an engine oil, said process comprising adding to the engine oil a composition according to the present invention.

Another aspect of the present invention is a process of preparation of a lubricant, said process comprising adding to the lubricant a composition according to the present invention.

Another aspect of the present invention is a process of preparation of a metal working fluid, said process comprising adding to the metal working fluid a composition according to the invention.

Another aspect of the present invention is a process of preparation of an oil field composition, said process comprising adding to the oil field composition a composition according to the invention.

The following examples are given in order to provide a person skilled in the art with a sufficiently clear and complete explanation of the present invention, but should not be considered as limiting the essential aspects of its subject, as set out in the preceding portions of this description.

EXAMPLES

The first part of the Examples section refers to the preparation of the compositions of the present invention.

The second part of the Examples section refers to the performance in industrial applications of the compositions of the present invention.

1. Preparation of the Composition Comprising an Ether Carboxylic Acid Compound According to the Invention

Example 1 (Comparative C1)

692 grams (1 mol) of a cetyl/stearyl fatty alcohol alkoxylated with 6 propoxylated units and 2 ethoxylated units were introduced in a double wall reactor. The reactor was heated to 105° C. and pressure was set to 20 mbar. The mixture was stirred (600 rpm), and 126 grams (1 mol) of an aqueous solution (75%) of monochloroacetic acid (MCA) and 160 grams (2 mol) of an aqueous solution (50%) of sodium hydroxide (NaOH) were introduced independently and simultaneously into the reactor. Monochloroacetic acid is introduced into the reactor with a dosing speed of 30 mmol/min and sodium hydroxide is introduced into the reactor with a dosing speed of 60 mmol/min. Water was removed and collected in downstream cooling traps. After the 33 minutes reaction time was elapsed an aging step of 30 minutes was performed. Then warm hydrochloric acid (30%) was added to the reaction mixture until a pH lower than 3 was obtained. The reaction mixture was transferred to a heated separation vessel, and additional water was added to reach a NaCl concentration of around 20% in the water layer. A phase separation was carried out without stirring at a temperature between 100-105° C. After separation of the aqueous lower phase, 702 grams of a light yellow liquid were obtained.

Example 2 (Comparative C2)

692 grams (1 mol) of a cetyl/stearyl fatty alcohol alkoxylated with 6 propoxylated units and 2 ethoxylated units were introduced in a double wall reactor. The reactor was heated to 105° C. and pressure was set to 20 mbar. The mixture was stirred (600 rpm), and 126 g (1 mol) of an aqueous solution (75%) of monochloroacetic acid (MCA) and 160 g (2 mols) of an aqueous solution (50%) of sodium hydroxide were introduced independently into the reactor. Monochloroacetic acid is introduced into the reactor with a dosing speed of 30 mmol/min and sodium hydroxide is introduced into the reactor with a dosing speed of 60 mmol/min. The addition of NaOH started earlier (3.3 minutes before starting addition of monochloroacetic acid), and 10% wt. of total NaOH was fed into the reactor during the early feeding step. Water was removed and collected in downstream cooling traps. After the 33 minutes reaction time was elapsed, an aging step of 30 minutes was performed. Then warm hydrochloric acid (30%) was added to the reaction mixture until a pH lower than 3 was obtained. The reaction mixture was transferred to a heated separation vessel and additional water was added to reach a had concentration of around 20% in the water layer. A phase separation was carried without stirring at a temperature between 100-105° C. After separation of the aqueous lover phase, 712 g of product were obtained as a light yellow liquid.

Example 3 (Comparative C3)

692 grams (1 mol) of a cetyl/stearyl fatty alcohol alkoxylated with 6 propoxylated units and 2 ethoxylated units were introduced in a double wall reactor. The reactor was heated to 105° C. and pressure was set to 20 mbar. The mixture was stirred (600 rpm), and 126 g (1 mol) of an aqueous solution (75%) of monochloroacetic acid (MCA) and 169 g (2,1 mol) of an aqueous solution (50%) of sodium hydroxide were introduced independently and simultaneously into the reactor. Monochloroacetic acid is introduced into the reactor with a dosing speed of 30 mmol/min and sodium hydroxide is introduced into the reactor with a dosing speed of 63 mmol/min. Water was removed and collected in downstream cooling traps. After the 33 minutes reaction time was elapsed, an aging step of 30 minutes was performed. Then warm hydrochloric acid (30%) was added to the reaction mixture until a pH lower than 3 was obtained. The reaction mixture was transferred to a heated separation vessel and additional water was added to reach a NaCl concentration of around 20% in the water layer. A phase separation was carried without stirring at a temperature between 100-105° C. After separation of the aqueous lower phase, 709 g of product were obtained as a light yellow liquid.

Example 4 (Comparative C4)

692 grams (1 mol) of a cetyl/stearyl fatty alcohol alkoxylated with 6 propoxylated units and 2 ethoxylated units were introduced in a double wall reactor. The reactor was heated to 105° C. and pressure was set to 20 mbar. The mixture was stirred (600 rpm), and 126 g (1 mol) of an aqueous solution (75%) of monochloroacetic acid (MCA) and 167 g (2.075 mol) of an aqueous solution (50%) of sodium hydroxide were introduced independently into the reactor. Monochloroacetic acid is introduced into the reactor with a dosing speed of 30 mmol/min and sodium hydroxide is introduced into the reactor with a dosing speed of 62, mmol/min. The addition of NaOH started earlier (5 minutes before starting the addition of monochloroacetic acid), and 15% wt. of total NaOH was fed into the reactor during the early feeding step. Water was removed and collected in downstream cooling traps. After the 33 minutes reaction time was elapsed, an aging step of 30 minutes was performed. Then warm hydrochloric acid (30%) was added to the reaction mixture until a pH lower than 3 was obtained. The reaction mixture was transferred to a heated separation vessel and additional water was added to reach a NaCl concentration of around 20% in the water layer. A phase separation was carried out without stirring at a temperature between 100-105° C. After separation of the aqueous lower phase, 729 g of product were obtained as a light yellow liquid.

Example 5 (Comparative 5)

The procedure of Example 3 (Comparative 3) is repeated using a cetyl/stearyl fatty alcohol alkoxylated with 9 ethoxylated units as starting materials of the synthesis.

Example 6 (Comparative 6)

The procedure of Example 4 (Comparative 4) is repeated using a cetyl/stearyl fatty alcohol alkoxylated with 9 ethoxylated units as starting materials of the synthesis.

Example 7 (According to the Invention A)

692 grams (1 mol) of a cetyl/stearyl fatty alcohol alkoxylated with 6 propoxylated units and 2 ethoxylated units were introduced in a double wall reactor. The reactor was heated to 105° C. and pressure was set to 20 mbar. The mixture was stirred (600 rpm) and 126 g (1 mol) of an aqueous solution (75%) of monochloroacetic acid (MCA) and 173 g (2.15 mol) of an aqueous solution (50%) of sodium hydroxide were introduced independently into the reactor. Monochloroacteic acid is introduced into the reactor with a dosing speed of 30 mmol/min and sodium hydroxide is introduced into the reactor with a dosing speed of 64.5 mmol/min. The addition of NaOH started earlier (5 minutes before starting the addition of monochloroacetic acid), and 15% wt. of total NaOH was fed into the reactor during the early feeding step. Water was removed and collected in downstream cooling traps. After the 33 minutes reaction time was elapsed, an aging step of 30 minutes was performed. Then warm hydrochloric acid (30) was added to the reaction mixture until a pH lower than 3 was obtained. The reaction mixture was then transferred to a heated separation vessel and additional water was added to reach a NaCl concentration of around 20% in the water layer. A phase separation was carried out without stirring at a temperature between 100-105° C. After separation of the aqueous lower phase, 720 g of product were obtained as a light yellow liquid.

Example 8 (According to the Invention B)

692 grams (1 mol) of a cetyl/stearyl fatty alcohol alkoxylated with 6 propoxylated units and 2 ethoxylated units were introduced in a double wall reactor. The reactor was heated to 105° C. and pressure was set to 20 mbar. The mixture was stirred (600 rpm) and 126 g (1 mol) of an aqueous solution (75%) of monochloroacetic acid (MCA) and 179 g (2.225 mol) of an aqueous solution (50%) of sodium hydroxide were introduced independently into the reactor. Monochloroacetic acid is introduced into the reactor with a dosing speed of 30 mmol/min and sodium hydroxide is introduced into the reactor with a dosing speed of 66.8 mmol/min. The addition of NaOH started earlier (5 minutes before starting the addition of monochloroacetic acid), and 15% wt. of total NaOH was fed into the reactor during the early feeding step. Water was removed and collected in downstream cooling traps. After the 33 minutes reaction time was elapsed, an aging step of 30 minutes was performed. Then warm hydrochloric acid (30%) was added to the reaction mixture until a pH lower than 3 was obtained. The reaction mixture was then transferred to a heated separation vessel and additional water was added to reach a NaCl concentration of around 20% in the water layer. A phase separation was carried out without stirring at a temperature between 100-105° C. After separation of the aqueous lower phase, 720 g of product were obtained as a light yellow liquid.

Example 9 (According to the Invention C)

The procedure of Example 7 (Invention A) is repeated using a cetyl/stearyl fatty alcohol alkoxylated with 9 ethoxylated units as starting materials of the synthesis.

Example 10 (According to the Invention D)

The procedure of Example 8 (Invention B) is repeated using a cetyl/stearyl fatty alcohol alkoxylated with 9 ethoxylated units as starting material of the synthesis.

Table 1 summarizes all the prepared compositions (molar ratio NaOH:MCA, initial feeding of NaOH), as well as the conversion degree.

TABLE 1

| Example | Molar ratio NaOH:MCA | Pre-run NaOH (%) | Conversion Degree |
|---|---|---|---|
| C1 | 2:1 | — | 27.1 |
| C2 | 2:1 | 10 | 40.4 |
| C3 | 2.1:1 | — | 33.2 |
| C4 | 2.075:1 | 15 | 53.6 |
| C5 | 2.1:1 | — | 34.6 |
| C6 | 2.075:1 | 15 | 52.9 |
| A | 2.15:1 | 15 | 80.2 |
| B | 2.225:1 | 15 | 78.6 |
| C | 2.15:1 | 15 | 77.4 |
| D | 2.225:1 | 15 | 81.9 |

Table 2 summarizes the Chemical Oxygen Demand (COD) for Examples C1 to C4, A and B:

TABLE 2

| | C1 | C2 | C3 | C4 | A | B |
|---|---|---|---|---|---|---|
| COD [mg $O_2$/L] | 62000 | 54000 | 56000 | 47000 | 34000 | 40000 |

Content of Oxygen Demand was determined according to standard DIN 38409-H41, and it was measured in the aqueous phase after washing step.

2. Performance Industrial Applications of the Compositions of the Present Invention Relevant properties for industrial applications are lubricity and water hardness stability.

Lubricity can be determined using the TTT Tapping-Torque-Testsystem by Microtap for the compositions prepared in Examples 1 to 6. Detailed parameters for the TTT test device are listed in Table 3.

TABLE 3

| | |
|---|---|
| Depth [mm] | 8000 |
| Rotation speed [1/min.] | 800 |
| Torque [Ncm] | 400 |
| Thread | right |
| Returns [%] | 100 |
| Start conditions | manual |
| First slice pressure Fz | 5 |
| Lubrication tact | non |
| Relaxing | 0 |

For the torque test, 10 w/w % of Compositions of Examples were diluted in Marcol 52 (Exxon Mobil white oil). Also, blank comprising only oil was measured. The used equipment for the TTT-test was:

Testbar: AlZnMgCu01,5/3.4365/7075

Tool: TTT_M4F-NT HSSE

Table 4 summarizes the results obtained for the compositions of the Examples C1 to C4, A and B:

TABLE 4

| | Mean Torque [Ncm] |
|---|---|
| Marcol 52 | 94.3 |
| C1 | 97.0 |
| C2 | 95.0 |
| C3 | 94.6 |
| C4 | 93.3 |
| A | 91.2 |
| B | 92.4 |

From these results it can be seen that compositions according to the present invention show lower results in torque, therefore showing better results in lubricity as the blank or comparative examples.

Another relevant property for industrial applications is the water hardness stability. Table 5 shows the water hardness stability of compositions of Examples C5, C6, C and D.

TABLE 5

| Example | Water hardness stability [%] |
|---|---|
| C5 | 57.1 |
| C6 | 72.9 |
| C | 95.3 |
| D | 97.1 |

Water hardness stability is determined using DIN 51367/51368.

From these results it can be seen that compositions according to the invention show better water hardness stability.

The invention claimed is:

1. A process for preparing a composition comprising an ether carboxylic acid of Formula (I)

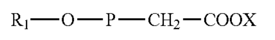

wherein $R_1$ is a linear or branched alkyl or alkenyl chain having from 1 to 30 carbon atoms, P comprises an average of n units of —$(CH_2CH_2O)$— and/or an average of m units of —$(CH_2CHR_2O)$— or —$(CHR_2CH_2O)$— and/or an average of q units of —$(CH_2CHR_3O)$— or —$(CHR_3CH_2O)$—, wherein n represents a number within the range of 0 to 50, m represents a number within the range of 0 to 50 and q represents a number within the range of 0 to 50, and the sum of n+m+q represents the average alkoxylation degree which corresponds to a number from 1 to 100; $R_2$ represents a —$CH_3$ group and $R_3$ represents a —$CH_2CH_3$ group; and X represents a hydrogen atom or a cation selected from the group consisting of alkali metals, alkaline earth metals, ammonium, alkylammoniums, and alkanolammoniums, the process comprising the steps of:

i. providing in a reactor an oxyalkylated alcohol compound of

Formula (II)

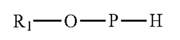

wherein $R_1$ and P have the values set forth in Formula (I);

ii. feeding an alkaline solution containing an alkali salt to the oxyalkylated alcohol compound of Formula (II); and iii. carboxyalkylating the oxyalkylated alcohol compound of Formula (II) with monochloroacetic acid, wherein the molar ratio between the monochloroacetic acid and an alkali salt in the alkaline solution is greater than 1:2.15 and up to 1:3.

2. The process of preparation according to claim 1, wherein from 5 to 50% by weight of the total amount of alkaline solution is fed to the reactor before the monochloroacetic acid is added.

3. The process of preparation according to claim 2, wherein the dosage time of feeding the alkaline solution before addition of the monochloroacetic acid takes from 5 to 50% of the total time of the feeding step (ii) and the carboxyalkylation step (iii).

4. The process of preparation according to claim 1, wherein the process further comprises the step of (iv) adding an acid after the carboxyalkylating step (iii) to convert the obtained ether carboxylic acid salt to a free ether carboxylic acid.

5. The process of preparation according to claim 4, wherein the process further comprises a washing step and/or a distillation step.

* * * * *